United States Patent
Yan et al.

(10) Patent No.: US 11,141,498 B2
(45) Date of Patent: Oct. 12, 2021

(54) PHOTO-OXIDATION REMOVAL OF ORGANIC CONTAMINATION FOR ENVIRONMENTAL SENSOR INTEGRATION

(71) Applicant: Apple Inc., Cupertino, CA (US)

(72) Inventors: Miaolei Yan, Santa Clara, CA (US); Michael K. Brown, Sunnyvale, CA (US); Richard Yeh, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/258,431

(22) Filed: Jan. 25, 2019

(65) Prior Publication Data

US 2020/0237940 A1 Jul. 30, 2020

(51) Int. Cl.
A61L 2/10 (2006.01)
G01N 33/00 (2006.01)
A61L 9/20 (2006.01)

(52) U.S. Cl.
CPC ............ *A61L 2/10* (2013.01); *G01N 33/0047* (2013.01); *A61L 9/20* (2013.01); *A61L 2202/16* (2013.01)

(58) Field of Classification Search
CPC ... A61L 2/10; A61L 9/205; A61L 9/20; A61L 2202/16; G01N 33/0047
See application file for complete search history.

(56) References Cited

U.S. PATENT DOCUMENTS

2006/0104858 A1* 5/2006 Potember ................ A61L 9/015
422/4
2006/0188389 A1* 8/2006 Levy ........................ A61L 2/24
422/24
2007/0217944 A1* 9/2007 Potember ................. A61L 9/14
422/4
2009/0129974 A1* 5/2009 McEllen ............... F04D 25/088
422/24
2015/0125355 A1* 5/2015 Lee ....................... B01D 53/007
422/186.3
2016/0000953 A1* 1/2016 Bettles ..................... A61L 2/24
250/455.11
2018/0161594 A1* 6/2018 Yehezkel ............. A61N 5/0624
2018/0264150 A1* 9/2018 Shur ...................... H04N 5/332
2019/0091738 A1* 3/2019 Chen ..................... B08B 7/0057
2019/0209725 A1* 7/2019 Henniges ................ A61L 2/208
2019/0298871 A1* 10/2019 Dobrinsky ................ A61L 2/10
2019/0328915 A1* 10/2019 Paul ..................... A61M 25/002

(Continued)

OTHER PUBLICATIONS https://en.wikipedia.org/wiki/Photon, retrieved Mar. 31, 2020. (Year: 2020).*

(Continued)

*Primary Examiner* — Wyatt A Stoffa
(74) *Attorney, Agent, or Firm* — Morgan, Lewis & Bockius LLP

(57) ABSTRACT

A portable communication device includes an apparatus for environmental sensing. The apparatus includes a housing, one or more environmental sensors and an optical source. The housing includes one or more ports for allowing air flow between the surrounding environment and a cavity of the housing. The environmental sensors are coupled to the housing and can sense an environmental agent included in the air flow. The optical source can illuminate the cavity of the housing to decompose unwanted organic compounds inside the port.

20 Claims, 4 Drawing Sheets

(56) References Cited

U.S. PATENT DOCUMENTS

| | | | |
|---|---|---|---|
| 2020/0000950 A1* | 1/2020 | Bohman | C01B 13/11 |
| 2020/0086283 A1* | 3/2020 | Tezuka | B01D 69/10 |
| 2020/0129972 A1* | 4/2020 | Ozaki | B01J 27/24 |
| 2020/0237947 A1* | 7/2020 | Brown | A61L 9/20 |

OTHER PUBLICATIONS https://support.apple.com/kb/SP808?locale=en_US (Year: 2020).*
"TE Sensor Solutions", published Mar. 2017 (Year: 2017).*

* cited by examiner

PHOTO-OXIDATION REMOVAL OF ORGANIC CONTAMINATION FOR ENVIRONMENTAL SENSOR INTEGRATION

TECHNICAL FIELD

The present description relates generally to sensor technology, and more particularly to photo-oxidation removal of organic contamination for environmental sensor integration.

BACKGROUND

Many mobile electronic devices are equipped with sensors and transducers that enable the devices to perform far more functionalities than communications. Media playing, photography, location detection, online shopping, social media, online banking, calendar and health applications such as heartbeat, blood pressure and blood oxygen level measurement are among the numerous applications that a smart mobile communication device can facilitate. Further, smart mobile communication devices (e.g., smartphones and smartwatches) can be equipped with environmental sensors, such as pressure sensors, humidity sensors and gas sensors.

Environmental sensors integrated into a mobile electronic device can offer novel features such as personal environmental detection and air quality monitoring. However, these devices are prone to organic residue accumulation, such as skin oils, dirt, body hair, etc. Such accumulations can contaminate the device housing and/or the sensor packaging that can produce interference signals and result in increasing sensor errors over an extended period of time. For example, miniature gas sensors rely on gas diffusion into the device housing to detect an ambient gas and to infer the ambient gas concentration. However, human skin lipids produce squalene, an oily organic compound that can stick to the housing surface and/or sensor packaging. Squalene reacts strongly with oxidizing gases (e.g., ozone and nitrogen oxides), which could significantly increase the errors of such sensors. Conventional methods may use a physical mesh (e.g., a stainless steel mesh) to prevent accumulation of dust or larger particles. The mesh, however, may not be effective toward oily organic compounds such as skin oil. Another mitigation scheme adopts active air flow (e.g., by using a pump or a fan) to compensate for analyte depletion. This scheme may not be ideal for mobile devices, given the size, power and noise impacts. Thus, methods suitable for mobile electronic devices are needed to remove organic contaminants and to clean the device housing and sensor packaging in order to ensure accuracy of the environmental sensors.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

Figure 1:
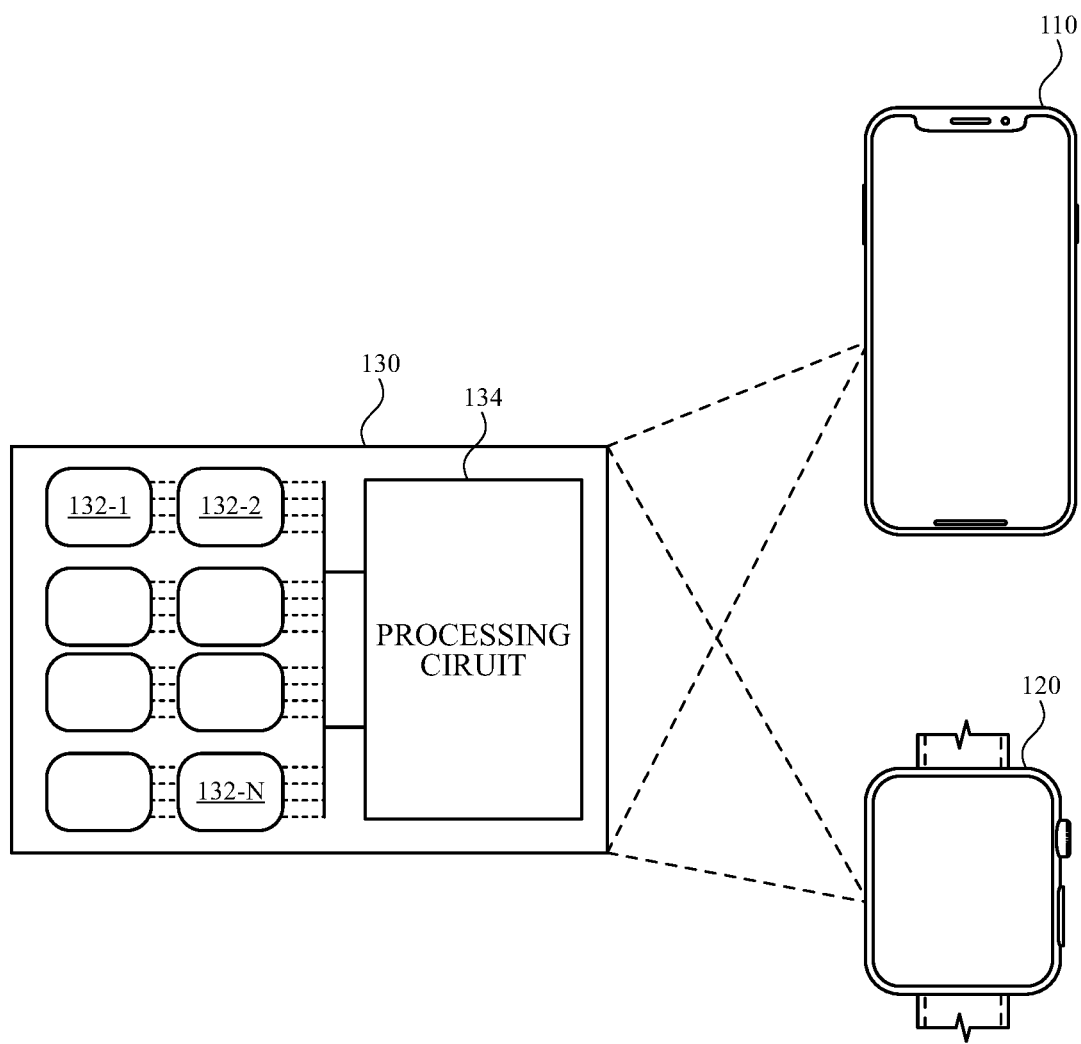
FIG. 1 is a high-level diagram illustrating examples of portable communication devices with environmental sensing capability, in accordance with one or more aspects of the subject technology.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in block diagram form in order to avoid obscuring the concepts of the subject technology.

In one or more aspects, the subject technology is directed to systems and methods to decompose organic contaminants inside product housing or near sensor packaging, in order to restore the clean environment needed for accurate readings of the integrated environmental sensors. In some implementations, the subject technology decomposes the organic contaminants by using ultraviolet (UV) light to illuminate the contaminants. The disclosed approach can be applied to a number of device platforms including mobile communication devices, such as smartphones and/or smartwatches or other wearable devices hosting environmental sensors. The environmental sensors can include miniature gas sensors such as sensors for volatile organic compounds (VOCs), ozone ($O_3$), nitrogen oxides (NOx), sulfur dioxide ($SO_2$), carbon monoxide (CO) and other environmental gases. A miniature sensor is understood to have dimensions smaller than a few millimeters and can be readily integrated into a smartphone or a smartwatch. The environmental sensors may also include relative humidity (RH) sensors and waterproof pressure sensors.

The disclosed solution can target the self-cleaning of both the interior surface of the device housing or mesh (e.g., aluminum, stainless steel), or the waterproof, air-permeable membranes made of materials such as expanded polytetrafluoroethylene (ePTFE) for individual sensors. In some implementations, the process of organic decomposition is based on UV induced photo-oxidation of organic molecules. The UV sources include UV light-emitting diodes (LEDs) in the UVA and/or UVB range, driven in continuous mode or duty cycling mode. UVA refers to UV light rays with wavelengths within a range of about 320-400 nm, and UVB refers to UV light rays with wavelengths within a range of about 260-320 nm. One or more UV LEDs can be employed at one or more UV wavelengths.

In some implementations, the UV LED can be packaged behind the waterproof, air-permeable membrane inside the sensor package, as discussed herein. In other implementations, the port geometry can be optimized in order to reduce stray light leakage outside the housing, for example, using light traps or light baffles.

In one or more aspects of the subject technology, a portable communication device includes an apparatus for environmental sensing. The apparatus includes a housing, one or more environmental sensors and an optical source. The housing includes one or more ports for allowing an air flow from an environment entering a cavity of the housing. The environmental sensors are coupled to the housing and can sense an environmental agent included in the air flow. The optical source can illuminate the cavity of the housing to decompose unwanted organic compounds.

In one or more aspects of the subject technology, a portable communication device includes an apparatus for environmental sensing that includes a housing, one or more environmental sensors and an optical source. The housing includes a port that allows an air flow to a cavity of the housing. The environmental sensors are coupled to the housing and can sense an environmental agent entering into the housing through a port of the housing. The optical source can illuminate the cavity of the housing to decompose unwanted organic compounds. The optical source is disposed outside the housing and on a sensor side of the housing.

In yet other aspects of the subject technology, a portable communication device includes an environmental sensing apparatus that includes one or more environmental sensors and a UV source. The environmental sensors are coupled to a housing and can sense an environmental agent in a cavity of the housing. The UV source illuminates the environmental sensors to decompose unwanted organic compounds in a photo-excitation process and to prevent the unwanted organic compounds from reaching the environmental sensors. The UV source and the one or more environmental sensors are packaged behind a waterproof membrane to reduce a footprint of the environmental sensing apparatus.

In some implementations, the environmental sensor can monitor a reaction product of the photo-oxidation process including volatile organic compounds (VOCs) and can determine a completion of a contamination removal process FIG. 1 is a high-level diagram illustrating examples of portable communication devices with environmental sensing capability, in accordance with one or more aspects of the subject technology. The environmental sensing capability of the subject technology can be integrated with a portable communication device such as a smartphone 110 or a smartwatch 120 to enable smartphone 110 or smartwatch 120 to sense environmental gases, for example, to recognize odors (smells) associated with various substances. Smartphone 110 and smartwatch 120 can communicate with other devices using one or more communication protocols such as Wi-Fi, cellular, Bluetooth, near-filed communications (NFC) and/or other communication protocols. The integration of the environmental sensing capability can make the portable communication device a platform with the capability of running an entire new dimension of applications, for instance, in health, safety, security, networking and other areas.

The portable communication device of the subject technology (e.g., the smartphone 110 or the smartwatch 120) includes an environmental sensing chip 130 that can communicate with other components of the portable communication device such as a central processor and memory (e.g., no-volatile or volatile memory) of the portable communication device. Environmental sensing chip 130 (hereinafter, "chip 130") may include a number of environmental sensors 132 (e.g., patches 132-1, 132-2 . . . 132-N) and a processing circuit 134. Chip 130 can be a semiconductor chip such as a silicon chip or a chip made of other semiconductor materials.

Environmental sensors 132 can be gas sensors that can detect many environmental gases including gases associated with chemical compounds or species that have aroma, odor or flavor. Each environmental sensor 132 is connected to a pair of electrodes. In some implementations, some parameters such as an electrode potential, a DC resistance, an AC impedance or other parameters of environmental sensors 132 can be changed as a result of being exposed to an environmental agent such as VOCs, $O_3$, $NO_x$, $SO_x$, CO, or humidity. The electrodes are continuously monitored and the measured parameters are reported to a central processing unit (CPU) of the portable communication device. In some implementations, the environmental sensor 132 can monitor a reaction product of the photo-oxidation process including volatile organic compounds (VOCs) and can determine a completion of a contamination removal process.

In some implementations, processing circuit 134 integrated on chip 130 and interfaced with environmental sensors 132 can provide biasing for and process the output signal from environmental sensors 132, as described in more detail herein. In one or more implementations, chip 130 may include a large number (e.g., 100-200) environmental sensors 132 (e.g., patches) and may occupy an area of about 5 mm×5 mm or smaller.

Figure 2:
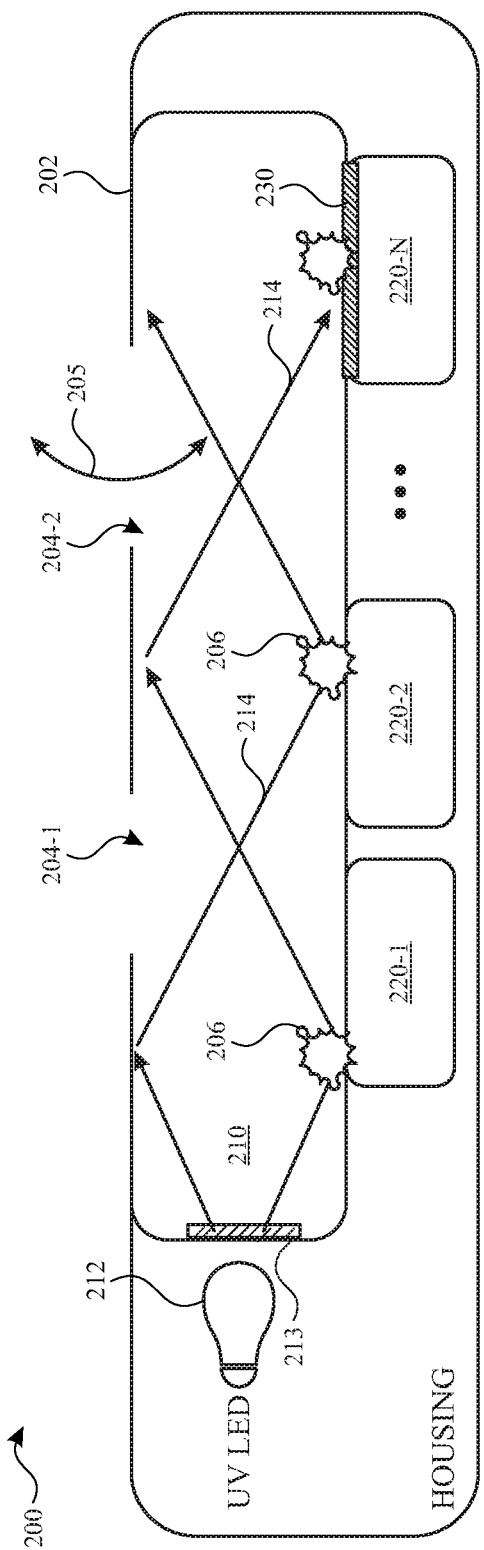
FIG. 2 is a diagram illustrating example apparatus with ultraviolet (UV) illumination for removal of organic contamination, in accordance with one or more aspects of the subject technology.

FIG. 2 is a diagram illustrating example apparatus 200 with UV illumination for removal of organic contamination, in accordance with one or more aspects of the subject technology. The apparatus 200 includes a housing 202, an optical source 212 as a number of environmental sensors (hereinafter, "sensors") 220 (e.g., 220-1, 220-2 . . . 220-N). Housing 202 has a cavity 210 and includes one or more ports 204 (e.g., 204-1 and 204-2). The ports 204 allow a flow of ambient air 205 from (into) the environment around the apparatus 200 into (from) cavity 210. In one or more implementations, one or more of the ports 204 can include a mesh such as a stainless steel mesh to block large particles from entering cavity 210. In some implementations, ports 204 may include a filter for removing particulate matters.

In some implementations, sensors 220 can be miniature sensors with dimensions of a few millimeters. Sensors 220 can be sensitive to environmental agents such as various environmental gases 206. For example, sensors 220 can be miniature gas sensors such as sensors for volatile organic compounds, ozone, nitrogen oxides, sulfur oxides, carbon monoxides, humidity and other environmental gases. One or more of sensors 220 can be interfaced (e.g., coupled) to housing 202 via a membrane 230. In some implementations, membrane 230 can be air permeable and/or waterproof. In one or more implementations, membrane 230 can be of ePTFE or other material with similar characteristics.

As explained above, environmental sensors may be prone to organic residue accumulation, such as skin oils, dirt, body hair, etc. Such accumulations can contaminate the device housing and/or the sensor packaging, which can produce interference signals and result in increasing sensor errors over an extended period of time. For example, human skin lipids produce squalene, an oily organic compound that can stick to the housing surface and/or sensor packaging. The subject technology provides solutions that can effectively prevent such contaminations, for example, by an optical illumination using a proper wavelength such as UV, for example, UVA and/or UVB. The UV rays can initiate a photo-oxidation process and decompose the contaminants such as unwanted organic compounds, for example, squalene and protect sensors from being contaminated. This can restore the clean environment inside cavity 210 that allows accurate readings of sensors 220.

In some implementations, optical source 212 can be a UV light source such as a UVA and/or a UVB light source. A UV source (e.g., optical source 212) can be implemented as an LED and can be driven in continuous mode or duty cycling mode. The light rays (e.g., UV light rays) from the optical source 212 (e.g., UV source) can experience multiple internal reflections 214 from the internal walls of housing 202, before reaching a sensor such as sensor 220-N. In one or more implementations, one or more of ports 204 can include light traps or light baffles that can reduce stray UV light leakage outside the cavity 210 of housing 202. In some implementations, cavity 210 includes an optical diffuser 213 that can evenly spread the UV light throughout cavity 210.

Figure 3:
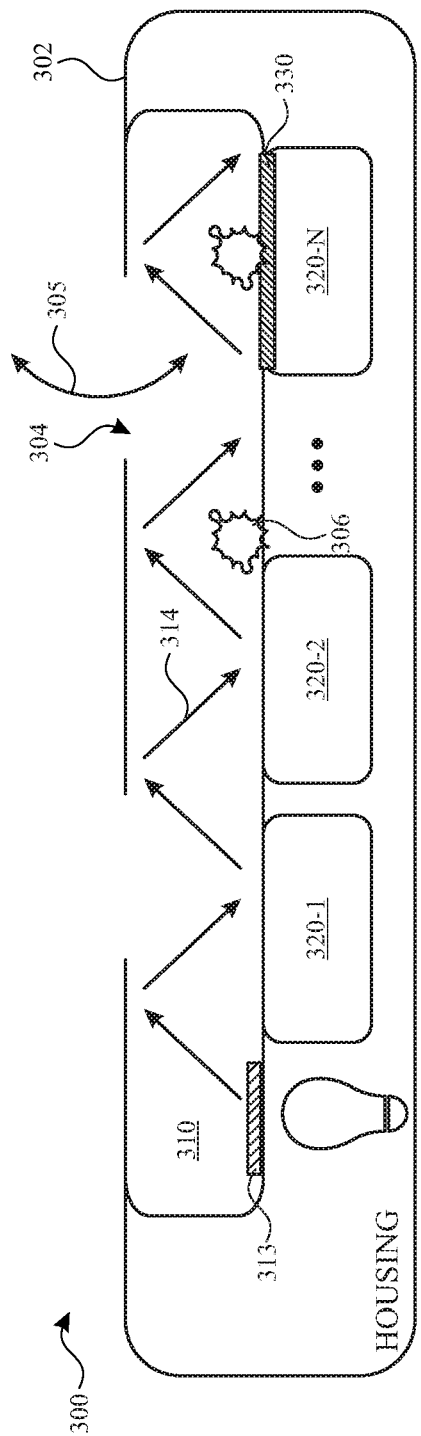
FIG. 3 is a diagram illustrating example apparatus having a UV light source on the environmental sensor side for removal of organic contamination, in accordance with one or more aspects of the subject technology.

FIG. 3 is a diagram illustrating example apparatus 300 having a UV light source on the environmental sensor side for removal of organic contamination, in accordance with one or more aspects of the subject technology. Apparatus 300 includes a housing 302, an optical source 312 and a number of environmental sensors (hereinafter, "sensors") 320 (e.g., 320-1, 320-2 . . . 320-N). Housing 302 has a cavity 310 and a port 304. The port 304 can facilitate a flow (e.g., in-and-out flow) of ambient air 305 from (into) the environment around the apparatus 300 into (from) cavity 310. In one or more implementations, port 304 can include a mesh (e.g., a stainless steel mesh) covering port 304 to block unwanted (e.g., large) particles from entering cavity 310. In some implementations, a filter can be used at the port 304 to remove particulate matters.

In one or more implementations, sensors 320 are miniature sensors (e.g., few mm size) and can be sensitive to environmental agents 306 such as various gases. For example, sensors 320 can be miniature gas sensors such as sensors for volatile organic compounds, ozone, nitrogen oxides, sulfur oxides, carbon monoxides, humidity and other environmental gases. One or more of sensors 320 can be interfaced (e.g., coupled) to housing 302 via a membrane 330. In some implementations, membrane 330 can be an air-permeable and/or a waterproof membrane, for example, made of ePTFE or other material with similar characteristics.

In some implementations, optical source 312 can be a UV light source such as a UVA and/or a UVB light source. The UV light source (e.g., optical source 312) can be realized using an LED and can be driven in continuous mode or duty cycling mode. In the implementation depicted in FIG. 3, optical source 312 is disposed outside cavity 310 and on the same side of housing 302 that sensors 320 are disposed. The light rays (e.g., UV light rays) from the optical source 312 (e.g., UV source) can enter cavity 310 and experience multiple internal reflections 314 from the internal walls of housing 302, before reaching a sensor such as sensor 320-N. In one or more implementations, port 304 can include light traps or light baffles that can reduce stray UV light leakage outside cavity 310 of housing 302. In some implementations, cavity 310 includes an optical diffuser 313 that can evenly spread the UV light throughout cavity 310. It is understood that disposing of optical source 312 outside cavity 310 can reduce a height footprint and manufacturing complexities of apparatus 300. In one or more implementations, multiple optical sources can be used to enhance the efficiency of organic contamination removal.

Figure 4:
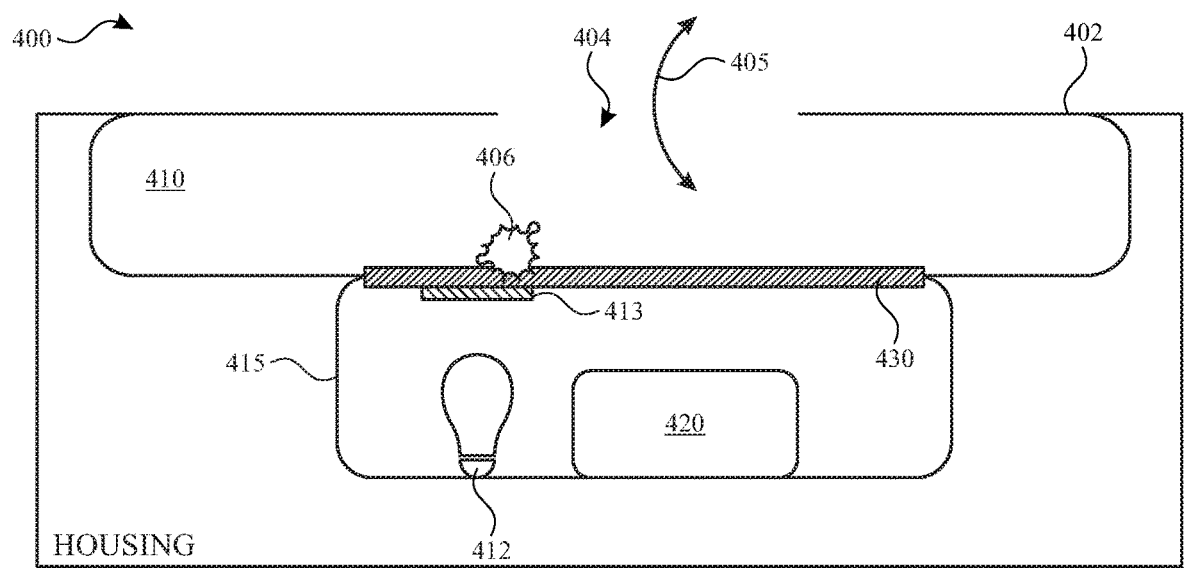
FIG. 4 is a diagram illustrating example apparatus having a UV light source packaged with the environmental sensor for removal of organic contamination, in accordance with one or more aspects of the subject technology.

FIG. 4 is a diagram illustrating example apparatus 400 having a UV light source packaged with the environmental sensor for removal of organic contamination, in accordance with one or more aspects of the subject technology. Example apparatus 400 is a compact and low-footprint implementation and includes a housing 402 having a cavity 410 and a sensor package 415. Sensor package 415 is interfaced with housing 402 using a membrane 430, which can be an air-permeable and/or waterproof membrane made, for example, ePTFE.

Housing 402 includes a port 404 to allow air flow 405 between cavity 410 and the surrounding environment. In some implementations, sensor package 415 includes an optical diffuser 413 that can evenly spread the UV light throughout sensor package 415. In one or more implementations, cavity 410 can be filled with a UV light-diffusing material. Sensor package 415 includes an environmental sensor 420 and an optical source (e.g., a UV light source) 412 illuminating inside sensor package 415 including environmental sensor 420 and membrane 430 to remove (e.g., by decomposing) unwanted organic compounds to prevent the unwanted organic compounds from reaching environmental sensor 420. In one or more implementations, sensor package 415 can be filled with a diffusing material that can evenly spread UV light rays.

In one or more implementations, environmental sensor 420 is a miniature (e.g., few mm size) environmental sensor that is sensitive to environmental agents 406 such as volatile organic compounds, ozone, nitrogen oxides, sulfur oxides, carbon monoxides, or humidity. The integration of optical source 412 with environmental sensor 420 with sensor package 415 reduces the footprint of apparatus 400 and allows using the apparatus 400 in more compact consumer electronic devices such as portable communication devices (e.g., smartphones and smartwatches).

Figure 5:
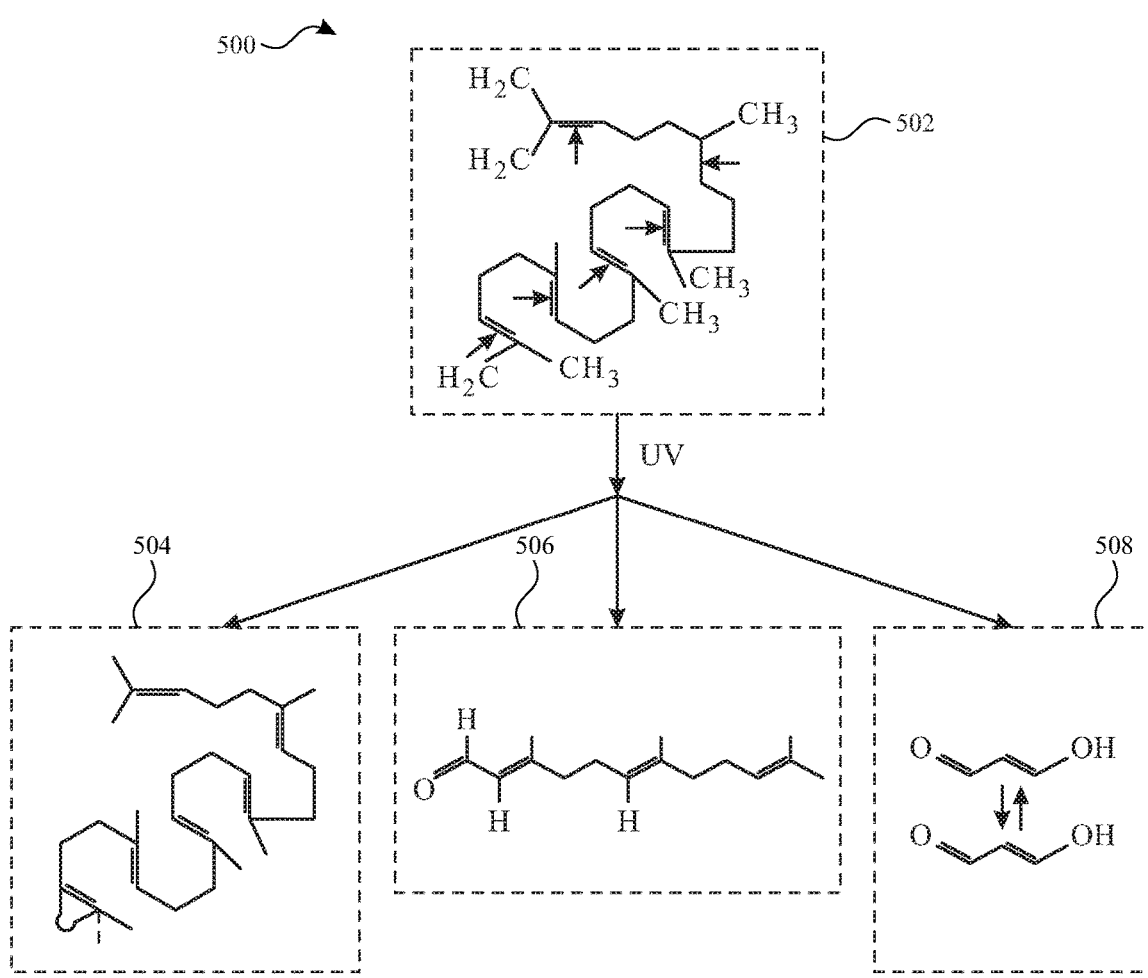
FIG. 5 is a diagram illustrating a chemical structure of squalene and its byproducts as a result of exposure to UV light.

FIG. 5 is a diagram illustrating a chemical structure 500 of squalene and its byproducts as a result of exposure to UV light. Squalene is an oily organic compound found in human skin lipids that can stick to the housing surface and/or environmental sensor packaging. Squalene can react strongly with oxidizing gases (e.g., ozone and nitrogen oxides), which can significantly increase the errors in environmental sensor measurements. The UV light rays can initiate a photo-oxidation process, which results in decomposition of squalene. Upon reaction with UV light, squalene, shown with its chemical formula 502, is decomposed into three byproducts 504, 506 and 508, as shown in FIG. 5 that may not be hazardous to environmental sensors.

Figure 6:
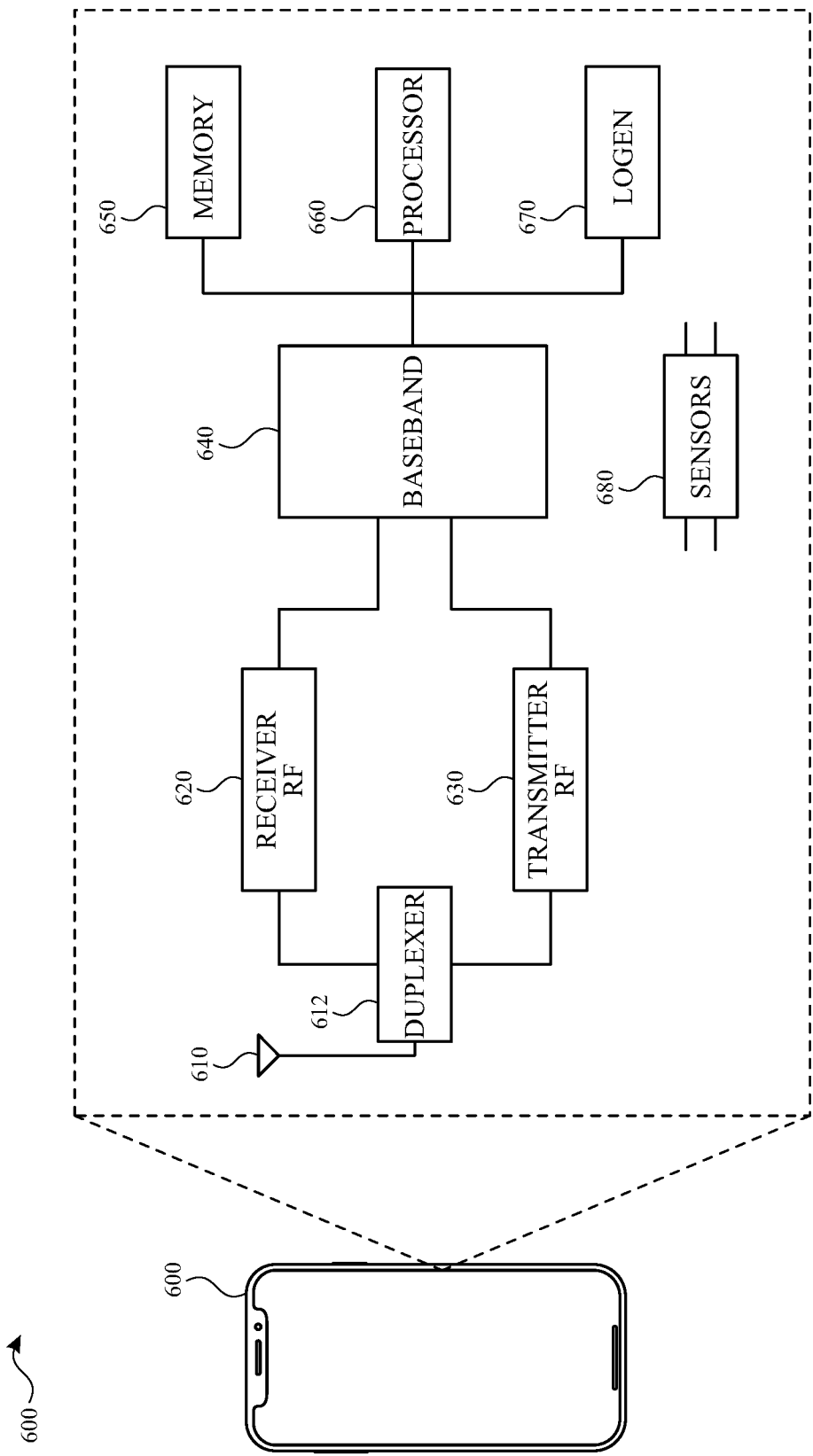
FIG. 6 is a block diagram illustrating an example wireless communication device, within which one or more environmental sensors of the subject technology can be integrated.

FIG. 6 is a block diagram illustrating an example wireless communication device 600, within which one or more environmental sensors of the subject technology can be integrated. The wireless communication device 600 may comprise a radio-frequency (RF) antenna 610, a duplexer 612, a receiver 620, a transmitter 630, a baseband processing module 640, a memory 650, a processor 660, a local oscillator generator (LOGEN) 670 and one or more sensors 680. In various embodiments of the subject technology, one or more of the blocks represented in FIG. 6 may be integrated on one or more semiconductor substrates. For example, the blocks 620-670 may be realized in a single semiconductor chip or a single system on a semiconductor chip, or may be realized in a multi-semiconductor chip semiconductor chipset.

The receiver 620 may comprise suitable logic circuitry and/or code that may be operable to receive and process signals from the RF antenna 610. The receiver 620 may, for example, be operable to amplify and/or down-convert received wireless signals. In various embodiments of the subject technology, the receiver 620 may be operable to cancel noise in received signals and may be linear over a wide range of frequencies. In this manner, the receiver 620 may be suitable for receiving signals in accordance with a variety of wireless standards, Wi-Fi, WiMAX, Bluetooth, and various cellular standards. In various embodiments of the subject technology, the receiver 620 may not require any surface-acoustic wave (SAW) filters and few or no off-semiconductor chip discrete components such as large capacitors and inductors.

The transmitter 630 may comprise suitable logic circuitry and/or code that may be operable to process and transmit signals from the RF antenna 610. The transmitter 630 may, for example, be operable to up-convert baseband signals to RF signals and amplify RF signals. In various embodiments of the subject technology, the transmitter 630 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 630 may be operable to provide signals for further amplification by one or more power amplifiers.

The duplexer 612 may provide isolation in the transmit band to avoid saturation of the receiver 620 or damaging parts of the receiver 620, and to relax one or more design requirements of the receiver 620. Furthermore, the duplexer 612 may attenuate the noise in the receive band. The duplexer 612 may be operable in multiple frequency bands of various wireless standards.

The baseband processing module 640 may comprise suitable logic, circuitry, interfaces, and/or code that may be operable to perform processing of baseband signals. The baseband processing module 640 may, for example, analyze received signals and generate control and/or feedback signals for configuring various components of the wireless communication device 600, such as the receiver 620. The baseband processing module 640 may be operable to encode, decode, transcode, modulate, demodulate, encrypt, decrypt, scramble, descramble, and/or otherwise process data in accordance with one or more wireless standards.

The processor 660 may comprise suitable logic, circuitry, and/or code that may enable processing data and/or controlling operations of the wireless communication device 600. In this regard, the processor 660 may be enabled to provide control signals to various other portions of the wireless communication device 600. The processor 660 may also control transfers of data between various portions of the wireless communication device 600. Additionally, the processor 660 may enable implementation of an operating system or otherwise execute code to manage operations of the wireless communication device 600.

The memory 650 may comprise suitable logic, circuitry, and/or code that may enable storage of various types of information such as received data, generated data, code, and/or configuration information. The memory 650 may comprise, for example, RAM, ROM, flash, and/or magnetic storage. In various embodiments of the subject technology, information stored in the memory 650 may be utilized for configuring the receiver 620 and/or the baseband processing module 640.

The local oscillator generator (LOGEN) 670 may comprise suitable logic, circuitry, interfaces, and/or code that may be operable to generate one or more oscillating signals of one or more frequencies. The LOGEN 670 may be operable to generate digital and/or analog signals. In this manner, the LOGEN 670 may be operable to generate one or more clock signals and/or sinusoidal signals. Characteristics of the oscillating signals such as the frequency and duty cycle may be determined based on one or more control signals from, for example, the processor 660 and/or the baseband processing module 640.

In operation, the processor 660 may configure the various components of the wireless communication device 600 based on a wireless standard according to which it is desired to receive signals. Wireless signals may be received via the RF antenna 610 and amplified and down-converted by the receiver 620. The baseband processing module 640 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device 600, data to be stored to the memory 650, and/or information affecting and/or enabling operation of the wireless communication device 600. The baseband processing module 640 may modulate, encode, and perform other processing on audio, video, and/or control signals to be transmitted by the transmitter 630 in accordance with various wireless standards.

The one or more sensors 680 may include the sensors 132 of FIG. 1. The sensors 132 of the subject technology can be readily integrated into the wireless communication device 600, in particular when the wireless communication device 600 is a smartphone or a smartwatch. The wireless communication device 600 can benefit from the disclosed photo-oxidation removal of organic contamination using a UV light source, as discussed above with respect to the apparatuses of FIGS. 2-4.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

The predicate words "configured to", "operable to" and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "example" is used herein to mean "serving as an example or illustration." Any aspect or design described herein as "example" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A portable communication device, the device comprising:
    an apparatus for environmental sensing comprising:
        a housing including one or more ports for allowing an air flow between a surrounding environment and a cavity of the housing;
        one or more environmental sensors coupled to the housing and configured to sense an environmental agent included in the air flow, wherein the one or more environmental sensors are miniature sensors, and wherein the one or more environmental sensors are further configured to monitor a reaction product of a photo-oxidation process and to determine a completion of a contamination removal process; and
        an optical source illuminating the cavity of the housing to decompose unwanted organic compounds.

2. The device of claim 1, further comprising an air-permeable membrane between the one or more environmental sensors and the housing.

3. The device of claim 2, wherein the air-permeable membrane comprises a waterproof membrane, wherein the air-permeable membrane comprises expanded polytetrafluoroethylene (ePTFE).

4. The device of claim 2, wherein the optical source comprises an ultraviolet (UV) source, wherein the UV source comprises a UV light-emitting diode configured to produce UVA or UVB spectra, and wherein the UV source is configured to initiate the photo-oxidation process to decompose unwanted organic compounds.

5. The device of claim 1, wherein the cavity of the housing includes an optical diffuser to evenly spread UV light, and wherein the reaction product of the photo-oxidation process comprises volatile organic compounds (VOCs).

6. The device of claim 4, wherein the UV source is disposed inside the cavity of the housing, and wherein the UV source is arranged to allow UV light rays from the UV source to experience multiple internal reflections from an inner surface of the housing before reaching the environmental sensor.

7. The device of claim 1, wherein the environmental sensor comprises a miniature gas sensor or a pressure sensor.

8. The device of claim 1, wherein the environmental agent comprises at least one of volatile organic compounds (VOCs), ozone, nitrogen oxides, sulfur oxides, carbon monoxide, or humidity.

9. The device of claim 1, wherein the one or more ports include a mesh, wherein the mesh comprises a stainless mesh.

10. The device of claim 1, wherein the one or more ports include a filter for removing particulate matter.

11. The device of claim 1, wherein the one or more ports are configured to reduce stray UV light leakage outside the cavity of the housing by using a light trap or a light baffle.

12. A portable communication device, the device comprising:
    an apparatus for environmental sensing comprising:
        a housing including a port, wherein the port is configured to allow an air flow to and from a cavity of the housing;
        one or more environmental sensors coupled to the housing and configured to sense an environmental agent entered into the housing, wherein the one or more environmental sensors are miniature sensors, and wherein the one or more environmental sensors are further configured to monitor a reaction product of a photo-oxidation process and to determine a completion of a contamination removal process; and
        an optical source configured to illuminate the cavity of the housing to decompose unwanted organic compounds,
        wherein the optical source is disposed outside the housing and on a sensor side of the housing.

13. The device of claim 12, further comprising a waterproof, air-permeable membrane between the one or more environmental sensors and the housing, wherein the waterproof, air-permeable membrane comprises expanded polytetrafluoroethylene (ePTFE).

14. The device of claim 12, wherein the optical source comprises an ultra-violet (UV) source, wherein the UV source comprises a UV light-emitting diode configured to produce UVA or UVB spectra.

15. The device of claim 14, wherein the UV source is configured to allow light rays from the UV source to experience multiple internal reflections from an inner surface of the housing before reaching the environmental sensor, wherein the cavity of the housing includes an optical diffuser to evenly spread the UV light.

16. The device of claim 14, wherein the environmental sensor comprises a miniature gas sensor or a pressure sensor, and the environmental agent comprises at least one of volatile organic compounds (VOCs), ozone, nitrogen oxides, sulfur oxides, carbon monoxides, or humidity.

17. A portable communication device, the device comprising:
    an environmental sensing apparatus comprising:
        one or more environmental sensors coupled to a housing and configured to sense an environmental agent in a cavity of the housing, wherein the one or more environmental sensors are miniature sensor, and wherein the one or more environmental sensors are further configured to monitor a reaction product of a photo-oxidation process and to determine a completion of a contamination removal process; and
        an ultra-violet (UV) source illuminating the one or more environmental sensors and configured to initiate the photo-oxidation process to decompose unwanted organic compounds and to prevent the one or more environmental sensors from being contaminated by the unwanted organic compounds,
wherein the UV source and the one or more environmental sensors are packaged behind a waterproof membrane to reduce a footprint of the environmental sensing apparatus.

18. The device of claim 17, wherein the housing includes one or more ports, wherein the one or more ports include a mesh or a particulate matter filter.

19. The device of claim 17, wherein the environmental sensor comprises a miniature gas sensor or a pressure sensor.

20. The device of claim 17, wherein the environmental agent comprises at least one of volatile organic compounds (VOCs), ozone, nitrogen oxides, sulfur oxides, carbon monoxide, or humidity.

* * * * *

UNITED STATES PATENT AND TRADEMARK OFFICE
CERTIFICATE OF CORRECTION

PATENT NO. : 11,141,498 B2  
APPLICATION NO. : 16/258431  
DATED : October 12, 2021  
INVENTOR(S) : Miaolei Yan et al.

Page 1 of 1

It is certified that error appears in the above-identified patent and that said Letters Patent is hereby corrected as shown below:

In the Claims

Column 10, Line 59 Claim 17 Replace "miniature sensor" with: --miniature sensors--.

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*